(12) United States Patent
Uchida et al.

(10) Patent No.: US 9,687,453 B2
(45) Date of Patent: *Jun. 27, 2017

(54) SOLID PHARMACEUTICAL COMPOSITION

(71) Applicant: KYORIN PHARMACEUTICAL CO., LTD., Tokyo (JP)

(72) Inventors: Hiroshi Uchida, Tochigi (JP); Masataka Hanada, Tochigi (JP); Yoshikazu Miyazaki, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/786,412

(22) PCT Filed: Apr. 24, 2014

(86) PCT No.: PCT/JP2014/002309
§ 371 (c)(1),
(2) Date: Oct. 22, 2015

(87) PCT Pub. No.: WO2014/174847
PCT Pub. Date: Oct. 30, 2014

(65) Prior Publication Data
US 2016/0074330 A1    Mar. 17, 2016

(30) Foreign Application Priority Data

Apr. 25, 2013 (JP) .................. 2013-092169

(51) Int. Cl.
| A61K 31/47 | (2006.01) |
| A61K 9/20 | (2006.01) |
| A61K 31/4709 | (2006.01) |
| A61K 9/28 | (2006.01) |

(52) U.S. Cl.
CPC .......... *A61K 9/2054* (2013.01); *A61K 9/2013* (2013.01); *A61K 9/2853* (2013.01); *A61K 9/2866* (2013.01); *A61K 31/4709* (2013.01)

(58) Field of Classification Search
USPC ....................................................... 514/312
See application file for complete search history.

(56) References Cited

U.S. PATENT DOCUMENTS

| 4,897,270 | A | 1/1990 | Deutsch et al. | |
| 6,727,243 | B1 | 4/2004 | Jennewein et al. | |
| 7,514,451 | B2 * | 4/2009 | Asahina ............... | C07D 401/04 514/300 |
| 8,106,072 | B2 * | 1/2012 | Asahina ............... | C07D 401/04 514/300 |
| 9,090,587 | B2 * | 7/2015 | Araya .................. | C07D 401/04 |
| 2004/0082593 | A1 | 4/2004 | Sommermeyer et al. | |
| 2004/0224014 | A1 | 11/2004 | Badwan et al. | |
| 2006/0281779 | A1 * | 12/2006 | Asahina ............... | C07D 471/04 514/300 |
| 2009/0176824 | A1 * | 7/2009 | Asahina ............... | C07D 401/04 514/300 |
| 2014/0288310 | A1 * | 9/2014 | Araya .................. | C07D 401/04 546/156 |
| 2015/0284361 | A1 * | 10/2015 | Araya .................. | C07D 401/04 514/312 |
| 2016/0067185 | A1 | 3/2016 | Uchida et al. | |

FOREIGN PATENT DOCUMENTS

| EP | 2 990 038 | 3/2016 |
| JP | 62-123118 | 6/1987 |
| JP | 2002-505290 | 2/2002 |
| JP | 2002-530338 | 9/2002 |
| JP | 2004-509921 | 4/2004 |
| JP | 2004-522782 | 7/2004 |
| JP | 2004-339198 | 12/2004 |
| JP | 2006-298811 | 11/2006 |
| WO | 99/44614 | 9/1999 |
| WO | 02/067943 | 9/2002 |
| WO | 2005/026147 | 3/2005 |
| WO | 2006/004028 | 1/2006 |
| WO | 2006/030826 | 3/2006 |
| WO | 2006/059716 | 6/2006 |
| WO | 2013/069297 | 5/2013 |
| WO | 2013/145749 | 10/2013 |
| WO | 2013/145750 | 10/2013 |

OTHER PUBLICATIONS

Tome Li et al. (abstract of Phys Chem B. May 23, 2013;117(20):6116-28).*
International Preliminary Report on Patentability issued Oct. 27, 2015 in corresponding International (PCT) Application No. PCT/JP2014/002309.
International Search Report issued Jul. 15, 2014 in International (PCT) Application No. PCT/JP2014/002309.
Hamaura et al., "Decrease in Dissolution of Cefpodoxime Proxetil Tablets by Gel Formation and Its Improvement", Journal of Pharmaceutical Science and Technology, vol. 55, No. 3, 1995, pp. 175-182.
Hamaura, "Gel formation of cefpodoxime proxetil, basic antibiotic and its formulation design", Pharm Tech Japan, vol. 17, No. 4, 2001, pp. 619-632.
Extended European Search Report issued Jan. 20, 2017 in corresponding European Application No. 14789034.7.

* cited by examiner

Primary Examiner — Sabiha N Qazi
(74) Attorney, Agent, or Firm — Wenderoth, Lind & Ponack, L.L.P.

(57) ABSTRACT

[Problem] To provide a novel pharmaceutical composition which contains a medically active component and which can suppress delays in the release of said component due to gelling.
[Solution] This solid pharmaceutical composition contains a compound represented by general formula (1), or a salt thereof, a cellulosic excipient, and a salting-out agent.

15 Claims, 4 Drawing Sheets

SOLID PHARMACEUTICAL COMPOSITION

TECHNICAL FIELD

The present invention relates to a solid pharmaceutical composition which contains a compound represented by the general formula (1) or a salt thereof.

[Chemical Formula 1]

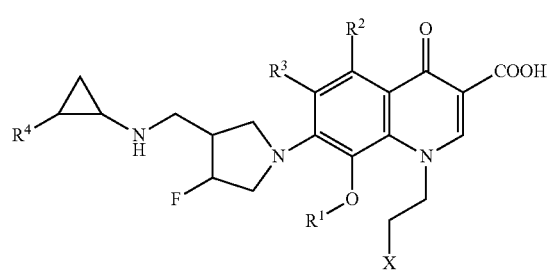

(1)

In the formula (1), $R^1$ represents an alkyl group having 1 to 3 carbon atoms of which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom.

BACKGROUND ART

Some active pharmaceutical ingredients which cause gelling under a certain condition have been known (Patent Literatures 1 to 7 and Non-Patent Literatures 1 and 2). In general, when a solid formulation is orally administrated, the solid formulation readily disintegrates in the gastrointestinal tract to dissolve an active pharmaceutical ingredient, so that the active pharmaceutical ingredient is absorbed into the body. However, when a solid formulation which contains an active pharmaceutical ingredient causing gelling is administrated, there is a problem in which the active pharmaceutical ingredient is gelled to delay the disintegration of the solid formulation, and delay the dissolution of the active pharmaceutical ingredient.

As conventional techniques of improving delay in disintegration due to gelling, a method of adding cyclodextrin to suppress gel formation or secure the water permeability of a gel layer (Non-Patent Literatures 1 and 2), a method of adding a disintegrant (Non-Patent Literature 1), a method of adding silicates (Patent Literatures 1 to 3), a method of making a drug finer and causing a carrier to adsorb the drug (Patent Literature 4), a method of rapidly breaking a film coating to disintegrate a drug-containing core before gelling (Patent Literature 5), a method using an acidic or basic additive (Patent Literature 6), and a method of achieving a molecular dispersion form in which a drug is dispersed in a polymer (Patent Literature 7) have been known.

As a formulation containing a quinolone carboxylic acid antimicrobial agent in which a main drug is stabilized, an oral composition which contains an acidic additive (Patent Literature 8) and an injection formulation which contains an acidic additive (Patent Literatures 9 and 10) have been known.

CITATION LIST

Patent Literature

Patent Literature 1: JP2006-298811
Patent Literature 2: WO2006/030826
Patent Literature 3: JP2002-505290
Patent Literature 4: JP2004-522782
Patent Literature 5: JPS62-123118
Patent Literature 6: WO2006/059716
Patent Literature 7: JP2002-530338
Patent Literature 8: JP2004-339198
Patent Literature 9: JP2004-509921
Patent Literature 10: WO2006/004028

Non-Patent Literature

Non-Patent Literature 1: Journal of Pharmaceutical Science and Technology, Japan, Vol. 55, No. 3 (1995), pp. 175-182
Non-Patent Literature 2: Pharm Tech Japan, vol. 17, No. 4 (2001) 87-100 (619-632).

SUMMARY OF INVENTION

Technical Problem

The present invention provides a novel pharmaceutical composition which can suppress delay in the release of a compound represented by the general formula (1) (hereinafter also referred to as compound of the formula (1)) or a salt thereof to be contained, due to gelling of the compound of the formula (1) or salt thereof.

[Chemical Formula 2]

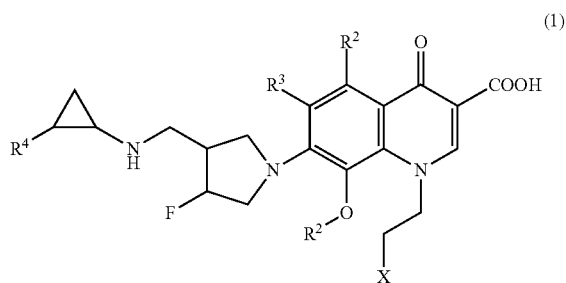

(1)

In the formula (1), $R^1$ represents an alkyl group having 1 to 3 carbon atoms of which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom.

Solution to Problem

The present inventors have found that when a solid composition which contains a compound of the formula (1) or a salt thereof is a composition which contains a cellulosic excipient and a salting-out agent, the dissolution property of the compound of the formula (1) or salt thereof is improved. Thus, the present invention has been accomplished.

The summary of the present invention is as follows:

[1] A solid pharmaceutical composition including a compound represented by the general formula (1) or a salt thereof, a cellulosic excipient, and a salting-out agent:

[Chemical Formula 3]

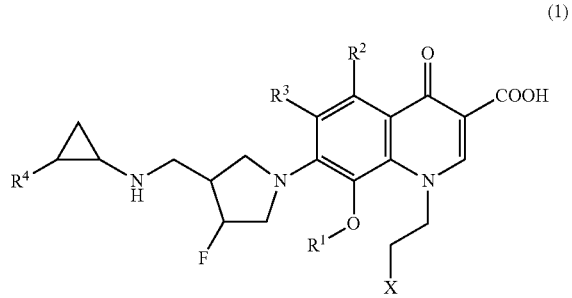

(1)

(wherein $R^1$ represents an alkyl group having 1 to 3 carbon atoms of which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom).

[2] The solid pharmaceutical composition according to [1], further containing an acidic substance of pH 3.5 or lower.

[3] The solid pharmaceutical composition according to [2], wherein the acidic substance has a solubility in water at 20° C. of less than 10%.

[4] The solid pharmaceutical composition according to [3], including, as the acidic substance having a solubility in water at 20° C. of less than 10%, one or two or more kinds of compounds selected from the group consisting of alginic acid, glutamic acid, aspartic acid, adipic acid, succinic acid, a methacrylic acid copolymer L, and fumaric acid.

[5] The solid pharmaceutical composition according to [2], wherein the acidic substance has a solubility in water at 20° C. of 10% or more.

[6] The solid pharmaceutical composition according to [5], including, as the acidic substance having a solubility in water at 20° C. of 10% or more, one or two or more kinds of compounds selected from the group consisting of glutamic acid hydrochloride, tartaric acid, citric acid, and malic acid.

[7] The solid pharmaceutical composition according to [5] or [6], wherein the acidic substance having a solubility in water at 20° C. of 10% or more is a compound different from the salting-out agent, and a ratio of the acidic substance is 0.001 parts by mass or more and 0.05 parts by mass or less relative to 1 part by mass of the compound represented by the general formula (1) or salt thereof.

[8] The solid pharmaceutical composition according to anyone of [1] to [7], including, as the salting-out agent, one or two or more kinds of compounds selected from the group consisting of an organic acid salt, an inorganic salt, and a salt of an amino acid.

[9] The solid pharmaceutical composition according to anyone of [1] to [7], including, as the salting-out agent, one or two or more kinds of compounds selected from the group consisting of a citric salt, a succinate, an acetate salt, a phosphoric salt, a carbonate, a sodium sulfate, a sodium sulfite, a sodium bisulfite, a calcium chloride, a sodium chloride, a potassium chloride, a magnesium chloride, a sodium hydroxide, and a glutamate.

[10] The solid pharmaceutical composition according to any one of [1] to [7], including, as the salting-out agent, one or two or more kinds of compounds selected from the group consisting of monobasic sodium citrate, dibasic sodium citrate, sodium citrate, disodium succinate, calcium acetate, sodium acetate, sodium dihydrogen phosphate, disodium monohydrogen phosphate, sodium metaphosphate, trisodium phosphate, monobasic potassium phosphate, dibasic potassium phosphate, sodium polyphosphate, sodium pyrophosphate, sodium carbonate, sodium bicarbonate, potassium carbonate, potassiumbicarbonate, ammonium carbonate, sodium sulfate, sodium sulfite, sodium bisulfite, calcium chloride, sodium chloride, potassium chloride, magnesium chloride, sodium hydroxide, L-glutamic acid hydrochloride, and monosodium L-glutamate monohydrate.

[11] The solid pharmaceutical composition according to any one of [1] to [7], including an organic acid salt as the salting-out agent.

[12] The solid pharmaceutical composition according to any one of [1] to [7], including a citric salt as the salting-out agent.

[13] The solid pharmaceutical composition according to any one of [1] to [7], including monobasic sodium citrate as the salting-out agent.

[14] The solid pharmaceutical composition according to [2] or any one of [5] to [7], including monobasic sodium citrate as the salting-out agent and glutamic acid hydrochloride as the acidic substance, and wherein a ratio of the glutamic acid hydrochloride is 0.02 parts by mass or more and 0.20 parts by mass or less relative to 1 part by mass of monobasic sodium citrate.

[15] The solid pharmaceutical composition according to [2], including glutamic acid hydrochloride as a compound which serves as the salting-out agent and the acidic substance.

[16] The solid pharmaceutical composition according to any one of [1] to [15], obtained by mixing the compound represented by the general formula (1) or salt thereof, the cellulosic excipient, and the salting-out agent and granulating the resulting mixture through a dry granulation method.

[17] The solid pharmaceutical composition according to any one of [1] to [16], including crystalline cellulose as the cellulosic excipient.

[18] The solid pharmaceutical composition according to any one of [1] to [17], including a hydrochloride as the salt of the compound represented by the general formula (1).

[19] The solid pharmaceutical composition according to [2], wherein the acidic substance is an acidic poorly water soluble substance.

[20] The solid pharmaceutical composition according to [19], including, as the acidic poorly water soluble substance, one or two or more kinds of compounds selected from the group consisting of alginic acid, glutamic acid, aspartic acid, adipic acid, a methacrylic acid copolymer L, and fumaric acid.

[21] The solid pharmaceutical composition according to [2], wherein the acidic substance is an acidic water-soluble substance.

[22] The solid pharmaceutical composition according to [21], including, as the acidic water-soluble substance, one or two or more kinds of compounds selected from the group consisting of glutamic acid hydrochloride, tartaric acid, citric acid, and malic acid.

[23] The solid pharmaceutical composition according to [21] or [22], wherein the acidic water-soluble substance is a compound different from the salting-out agent, and a ratio of the acidic water-soluble substance is 0.001 parts by mass or more and 0.05 parts by mass or less relative to 1 part by mass of the compound represented by the general formula (1) or salt thereof.

Advantageous Effects of Invention

The present invention can provide a novel solid pharmaceutical composition which includes the compound of the formula (1) or a salt thereof and can suppress delay in the release of the compound of the formula (1) or salt thereof due to gelling.

DESCRIPTION OF EMBODIMENTS

Figure 1:
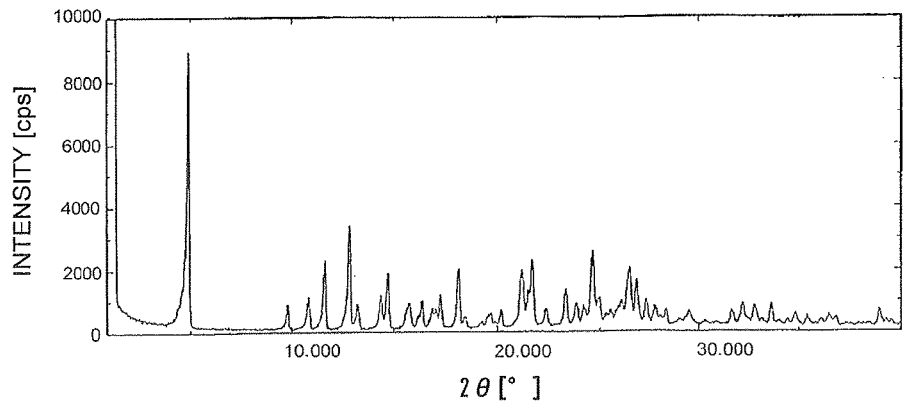
FIG. 1 is an X-ray powder diffraction pattern of 7-[(3S, 4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride A-type crystal.

Hereinafter, one of embodiments of the present invention will be described in detail.

The embodiment relates to a solid pharmaceutical composition which includes a compound represented by the general formula (1) or a salt thereof, a cellulosic excipient, and a salting-out agent. In the embodiment, the salting-out agent may be a compound acting as an acidic substance of pH 3.5 or lower described below. For example, the same compound as the salting-out agent may be contained as the acidic substance of pH 3.5 or lower.

The solid pharmaceutical composition herein represents a pharmaceutical composition including a solid component to be contained.

[Chemical Formula 4]

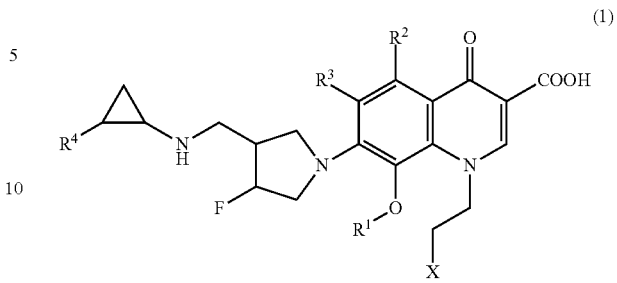

In the formula (1), $R^1$ represents an alkyl group having 1 to 3 carbon atoms, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom. One or two or more hydrogen atoms of the alkyl group having 1 to 3 carbon atoms represented by $R^1$ may be substituted with a halogen atom, an amino group, or a cyano group.

The "halogen atom" described herein represents a fluorine atom, a chlorine atom, a bromine atom, or an iodine atom. In the general formula (1), the halogen atom is preferably a fluorine atom. The "alkyl group having 1 to 3 carbon atoms" described herein is a methyl group, an ethyl group, a propyl group, or a 2-propyl group.

The compound of the formula (1) or salt thereof contained in the solid pharmaceutical composition of this embodiment can be produced, for example, through a method described in the pamphlet of WO2005/026147. The compound of the formula (1) contained in the solid pharmaceutical composition of this embodiment is preferably 7-[3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid, and more preferably 7-[(3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid.

It is preferable that the solid pharmaceutical composition of this embodiment contain a salt of the compound of the formula (1) from the viewpoint of improvement in solubility in water.

The salt of the compound of the formula (1) to be contained in the solid pharmaceutical composition of this embodiment is not particularly limited so long as it is a pharmaceutically acceptable salt. Examples of the salt of the compound of the formula (1) may include salts with inorganic acids such as hydrochloric acid, hydrobromic acid, sulfuric acid, and phosphoric acid, salts with organic acids such as maleic acid, fumaric acid, succinic acid, malic acid, malonic acid, methanesulfonic acid, toluenesulfonic acid, benzenesulfonic acid, lactic acid, oxalic acid, acetic acid, trifluoroacetic acid, and tartaric acid, and salts with metals such as sodium, potassium, magnesium, calcium, aluminum, cesium, chromium, cobalt, copper, iron, zinc, platinum, and silver. Among these, a hydrochloride is particularly preferred from the viewpoint of stability of the compound. A hydrochloride of the compound of the formula (1) is excellent since decomposition of the compound due to light irradiation is unlikely to proceed and the degree of chemical decomposition is low even in storage under an acceleration test condition, as compared with the compound of the formula (1) in a free form and another salt of the compound of the formula (1). The salt of the compound of the formula (1) to be contained in the solid pharmaceutical composition of this embodiment is preferably 7-[3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride, and more preferably 7-[(3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride.

Among the 7-[(3S,4S)-3-{(cyclopropylamino)methyl}-4-fluoropyrolidin-1-yl}-6-fluoro-1-(2-fluoroethyl)-8-methoxy-4-oxo-1,4-dihydroquinoline-3-carboxylic acid hydrochlorides, a crystal (A-type crystal) having an X-ray powder diffraction pattern with peaks at diffraction angles $2\theta$ of 10.8, 12.9, and 24.7° ($2\theta \pm 0.2°$) is likely to be gelled. Therefore, when the solid pharmaceutical composition contains the A-type crystal, use of the technique according to this embodiment is useful. The X-ray powder diffraction pattern of the A-type crystal is shown in FIG. 1. For example, the A-type crystal can be produced through a method described in WO2013/069297.

The content of the compound of the formula (1) or salt thereof in the whole mass of the solid pharmaceutical composition is preferably 10% by mass or more and 70% by mass or less, more preferably 20% by mass or more and 60% by mass or less, particularly preferably 30% by mass or more and 50% by mass or less, and further preferably 35% by mass or more and 45% by mass or less.

When the solid pharmaceutical composition of this embodiment is a tablet, "the whole mass of the solid pharmaceutical composition" means the mass of the whole uncoated tablet. The "uncoated tablet" described herein means a tablet into which a raw material is pressed and which is in a state before forming a coating.

The solid pharmaceutical composition of this embodiment contains the compound of the formula (1) or salt thereof, a cellulosic excipient, and a salting-out agent.

The "cellulosic excipient" described herein is an excipient which contains cellulose or derivatives thereof as a component. As the cellulosic excipient, the solid pharmaceutical composition of this embodiment contains one or two or more kinds of crystalline cellulose, carmellose, carmellose calcium, carmellose sodium, croscarmellose sodium, carboxymethyl cellulose calcium, and low substituted hydroxypropylcellulose. Among these, it is preferable that the cellulosic excipient contained in the solid pharmaceutical composition of this embodiment be crystalline cellulose since the hardness of molded tablet is high. The content of the cellulosic excipient in the whole mass of the solid pharmaceutical composition is 10% by mass or more and 70% by mass or less, more preferably 20% by mass or more and 60% by mass or less, particularly preferably 25% by mass or more and 50% by mass or less, and further preferably 30% by mass or more and 40% by mass or less.

The "salting-out agent" described herein means a salt exhibiting a salting-out action. The "salting-out action" described herein is an action of preventing the formation of gel substance having high viscosity by contact of the compound of the formula (1) with water. This action may be caused by unstabilizing hydration generated between the compound of the formula (1) and water by the salting-out agent.

Examples of the "salting-out agent" contained in the solid pharmaceutical composition of this embodiment may include an organic acid salt, an inorganic salt, and a salt of amino acid.

Examples of the organic acid salt may include citric salts such as monobasic sodium citrate, dibasic sodium citrate, and sodium citrate, succinates such as disodium succinate, and acetate salts such as calcium acetate and sodium acetate.

Examples of the inorganic salt may include phosphoric salts such as sodium dihydrogen phosphate, disodium monohydrogen phosphate, sodium metaphosphate, trisodium phosphate, monobasic potassium phosphate, dibasic potassium phosphate, sodium polyphosphate, and sodium pyrophosphate, carbonates such as sodium carbonate, sodium bicarbonate, potassium carbonate, potassium bicarbonate, and ammonium carbonate, sodium sulfate, sodium sulfite, sodiumbisulfite, calcium chloride, sodium chloride, potassium chloride, magnesium chloride, and sodium hydroxide.

Examples of the salt of amino acid may include glutamates such as L-glutamic acid hydrochloride and monosodium L-glutamate monohydrate.

In the solid pharmaceutical composition of this embodiment, one or two or more kinds of the compounds may be contained as a salting-out agent. It is preferable that the salting-out agent contained in the solid pharmaceutical composition of this embodiment be an organic acid salt, particularly preferably a citric salt, and further preferably monobasic sodium citrate.

Since the gelling of the compound of the formula (1) or salt thereof is suppressed and the dissolution ratio is improved, it is preferable that the ratio of the salting-out agent (when two or more kinds of compounds acting as a salting-out agent are contained, the total amount thereof is used) in the solid pharmaceutical composition of this embodiment be 0.05 parts by mass or more and 0.50 parts by mass or less relative to 1 part by mass of the compound of the formula (1) or salt thereof. Furthermore, the ratio of the salting-out agent contained in the solid pharmaceutical composition of this embodiment is more preferably 0.05 parts by mass or more and 0.40 parts by mass or less relative to 1 part by mass of the compound of the formula (1) or salt thereof, further preferably 0.10 parts by mass or more and 0.30 parts by mass or less, and still further preferably 0.15 parts by mass or more and 0.25 parts by mass or less.

In addition to the compound of the formula (1) or salt thereof, the cellulosic excipient, and the salting-out agent, the solid pharmaceutical composition of this embodiment may contain another component, for example, an acidic substance of pH 3.5 or lower.

Among the salting-out agents, there is a compound which is a salting-out agent and an acidic substance of pH 3.5 or lower, such as glutamic acid hydrochloride. The acidic substance of pH 3.5 or lower contained in the solid pharmaceutical composition of this embodiment may be a compound acting as a salting-out agent. For example, the salting-out agent and the acidic substance of pH 3.5 or lower may be the same. Even when the solid pharmaceutical composition of this embodiment contains such a compound of pH 3.5 or lower as a salting-out agent, another compound that is an acidic substance of pH 3.5 or lower may be contained.

The compound of the formula (1) or salt thereof is decomposed, for example, by pressurization during a production process, to produce a compound represented by the following formula (2) or the like. When the solid pharmaceutical composition contains the acidic substance of pH 3.5 or lower, the decomposition of the compound of the formula (1) or salt thereof can be suppressed.

[Chemical Formula 5]

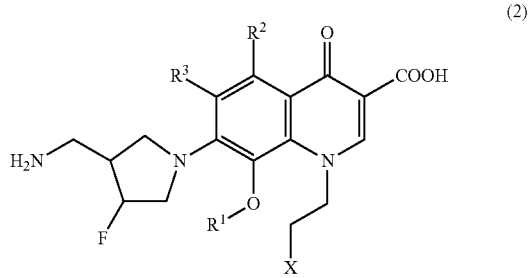

(2)

In the formula (2), $R^1$, $R^2$, $R^3$, and X are the same as the above-described definitions.

The solid pharmaceutical composition of this embodiment may contain an acidic substance having a solubility in water at 20° C. of less than 10%, an acidic substance having a solubility in water at 20° C. of 10% or more, or both the acidic substances as the acidic substance of pH 3.5 or lower.

The "acidic substance" described herein is a substance which is dissolved in water to generate hydrogen ions. "pH" described herein is a value obtained by measuring the pH of liquid (concentration: 2.5%), in which 50 mg of object substance is weighed, and dissolved or suspended in 1,950 μL of water, with a pH meter.

Examples of the acidic substance having a solubility in water at 20° C. of less than 10% and a pH of 3.5 or lower which may be contained in the solid pharmaceutical composition of this embodiment may include alginic acid, glutamic acid, aspartic acid, adipic acid, succinic acid, a methacrylic acid copolymer L, and fumaric acid. It is preferable that the acidic poorly water soluble substance having a solubility in water at 20° C. of less than 10% and a pH of 3.5 or lower which may be contained in the solid pharmaceutical be alginic acid, aspartic acid, adipic acid, succinic acid, or a methacrylic acid copolymer L, and particularly preferably alginic acid.

Examples of the acidic substance having a solubility in water at 20° C. of 10% or more and a pH of 3.5 or lower which may be contained in the solid pharmaceutical composition of this embodiment may include glutamic acid hydrochloride, tartaric acid, citric acid, and malic acid. It is preferable that the acidic substance having a solubility in water at 20° C. of 10% or more and a pH of 3.5 or lower which may be contained in the solid pharmaceutical composition of this embodiment be glutamic acid hydrochloride, tartaric acid, or citric acid, and particularly preferably glutamic acid hydrochloride.

From the viewpoint of suppressing the decomposition of the compound of the formula (1) or salt thereof, it is preferable that the ratio of the acidic substance of pH 3.5 or lower (when two or more kinds of acidic substances of pH 3.5 or lower are contained, the total amount thereof is used) in the solid pharmaceutical composition of this embodiment be 0.001 parts by mass or more relative to 1 part by mass of the compound of the formula (1) or salt thereof. Furthermore, the ratio of the acidic substance in the solid pharmaceutical composition of this embodiment is more preferably 0.001 parts by mass or more and 0.30 parts by mass or less relative to 1 part by mass of the compound of the formula (1) or salt thereof, and further preferably 0.001 parts by mass or more and 0.10 parts by mass or less.

When the acidic substance having a solubility in water at 20° C. of 10% or more and a pH of 3.5 or lower (in this case, the acidic substance is a compound different from a salting-out agent) is contained, the ratio of the acidic substance is particularly preferably 0.001 parts by mass or more and 0.05 parts by mass or less from the viewpoint of the resistance to the decrease in the dissolution ratio.

As described above, a compound which is contained as the acidic substance of pH 3.5 or lower may act as a salting-out agent in the solid pharmaceutical composition of this embodiment. Examples of the compound which serves as a salting-out agent and an acidic substance of pH 3.5 or lower may include glutamic acid hydrochloride. In the solid pharmaceutical composition of this embodiment, one or two or more kinds of the compounds may be contained. In this case, from the viewpoint of suppressing the decomposition of the compound of the formula (1) or salt thereof and improving the dissolution ratio, it is preferable that the ratio of the acidic substance of pH 3.5 or lower which serves as a salting-out agent be 0.15 parts by mass or more and 0.25 parts by mass or less relative to 1 part by mass of the compound of the formula (1) or salt thereof, and more preferably 0.15 parts by mass or more and 0.21 parts by mass or less.

When the solid pharmaceutical composition of this embodiment contains monobasic sodium citrate as a salting-out agent and glutamic acid hydrochloride as an acidic substance of pH 3.5 or lower, the ratio of glutamic acid hydrochloride is preferably 0.01 parts by mass or more relative to 1 part by mass of monobasic sodium citrate, more preferably 0.01 parts by mass or more and 0.5 parts by mass or less, and further preferably 0.02 parts by mass or more and 0.20 parts by mass or less.

When the solid pharmaceutical composition of this embodiment has a tablet form, the preferable content of the acidic substance of pH 3.5 or lower can be considered based on the mass of the whole uncoated tablet. In this case, the ratio of the acidic substance (when two or more kinds of acidic substances of pH 3.5 or lower are used, the total amount thereof is used) to the whole mass of the uncoated tablet is preferably 0.1% by mass or more and 10% by mass or less, and more preferably 0.1% by mass or more and 5% by mass or less. When the acidic substance having a solubility in water at 20° C. of 10% or more and a pH of 3.5 or less is contained, the ratio of the acidic substance is particularly preferably 0.2% by mass or more and 2% by mass or less from the view point of the resistance to the decrease in the dissolution ratio.

The "solubility in water" herein is a value obtained by calculation using the following equation (A) on the basis of the mass (g) of a solute that is dissolved in 100 g of water.

$$MW = \{C/(100+C)\} \times 100 \qquad (A)$$

In the equation (A), MW represents the solubility (%) in water and C represents the mass (g) of a solute that is dissolved in 100 g of water.

The solid pharmaceutical composition of this embodiment may contain an acidic poorly water soluble substance, an acidic water-soluble substance, or both the acidic substances as the acidic substance of pH 3.5 or lower.

The "acidic poorly water soluble substance" described herein means an acidic substance which is sparingly soluble in water, an acidic substance which is slightly soluble in water, an acidic substance which is very slightly soluble in water, or an acidic substance which is practically insoluble or insoluble in water. Examples of the acidic poorly water soluble substance of pH 3.5 or lower which may be contained in the solid pharmaceutical composition of this embodiment may include alginic acid, glutamic acid, aspartic acid, adipic acid, a methacrylic acid copolymer L, and fumaric acid. It is preferable that the acidic poorly water soluble substance of pH 3.5 or lower which may be contained in the solid pharmaceutical composition of this embodiment be alginic acid, aspartic acid, adipic acid, or a methacrylic acid copolymer L, and particularly preferably alginic acid.

The "acidic water-soluble substance" described herein means an acidic substance which is soluble in water, an acidic substance which is freely soluble in water, or an acidic substance which is very soluble in water. Examples of the acidic water-soluble substance of pH 3.5 or lower which may be contained in the solid pharmaceutical composition of this embodiment may include glutamic acid hydrochloride, tartaric acid, citric acid, and malic acid. It is preferable that the acidic water-soluble substance of pH 3.5 or lower which may be contained in the solid pharmaceutical composition of this embodiment be glutamic acid hydrochloride, tartaric acid, or citric acid, and particularly preferably glutamic acid hydrochloride.

When the acidic water-soluble substance of pH 3.5 or lower (in this case, the acidic substance is a compound different from a salting-out agent) is contained, the ratio of the acidic substance to the compound of the formula (1) or salt thereof is particularly preferably 0.001 parts by mass or more and 0.05 parts by mass or less from the viewpoint of the resistance to the decrease in the dissolution ratio.

Descriptive terms showing soluble properties herein other than those separately prescribed are in accordance with general notices in the Japanese Pharmacopoeia Sixteenth Edition. Specifically, a compound is converted into a powder, the powder is added to a solvent, and the mixture is mixed at 20±5° C. by strongly shaking for 30 seconds at intervals of 5 minutes. At that time, a degree of dissolution within 30 minutes is represented as the amount of solvent required to dissolve 1 g or 1 mL of solute. Meaning of each term is as described in Table 1. For example, "freely soluble in water" means that the amount of water required to dissolve 1 g or 1 mL of solute is 1 mL or more and less than 10 mL, and "very soluble in water" means that the amount of water required to dissolve 1 g or 1 mL of solute is less than 1 mL.

TABLE 1

| Descriptive term | Volume of solvent required for dissolving 1 g or 1 mL of solute |
| --- | --- |
| VERY SOLUBLE | Less than 1 mL |
| FREELY SOLUBLE | From 1 mL to less than 10 mL |
| SOLUBLE | From 10 mL to less than 30 mL |
| SPARINGLY SOLUBLE | From 30 mL to less than 100 mL |
| SLIGHTLY SOLUBLE | From 100 mL to less than 1000 mL |
| VERY SLIGHTLY SOLUBLE | From 1000 mL to less than 10000 mL |
| PRACTICALLY INSOLUBLE, OR INSOLUBLE | 10000 mL and over |

Examples of the solid pharmaceutical composition of this embodiment may include an oral composition. Specifically, the solid pharmaceutical composition of this embodiment can be formed into a solid oral formulation such as tablets, granules (fine granules), capsules, and powders, and preferably, can be formed into tablets.

The solid pharmaceutical composition of this embodiment can be produced in accordance with a common method corresponding to the dosage form, and the production method can be appropriately selected by those skilled in the art.

When the solid pharmaceutical composition of this embodiment is subjected to a granulation process for production, it is preferable that the granulation be in accordance with a dry granulation method. The "dry granulation method" described herein is a method in which a raw material powder is compression-molded, crushed, and classified into particles having appropriate size. According to the dry granulation method, granulation can be carried out without use of water. Therefore, the gelling of the compound of the formula (1) or salt thereof due to effects of water can be suppressed.

Hereinafter, the content of the solid pharmaceutical composition of this embodiment will be described more specifically with reference to one example of a method of producing the solid pharmaceutical composition of this embodiment as a tablet, and the scope of the present invention is not limited thereby. In description of one example of a production method in the following general production method, a case where the compound of the formula (1) or salt thereof, the cellulosic excipient, and the salting-out agent are added, and a case where the acidic substance of pH 3.5 or lower is further mixed are exemplified.

(General Production Method)
1. A, B, and C components shown below are mixed. In addition to the A, B, and C components, a D component may be mixed. The D component and the C component may be the same compound. To the powder obtained by the mixing, a lubricant such as stearic acid, a stearic acid salt (a salt with metal such as aluminum, potassium, sodium, calcium, and magnesium), and sodium laurylsulfate may be further added.
A component: a compound represented by the formula (1) or a salt thereof
B component: one or two or more kinds of cellulosic excipients selected from the group consisting of crystalline cellulose, carmellose, carmellose calcium, carmellose sodium, croscarmellose sodium, carboxymethyl cellulose calcium, and low substituted hydroxypropylcellulose
C component: one or two or more kinds of salting-out agents selected from the group consisting of citric salts such as monobasic sodium citrate, dibasic sodium citrate, and sodium citrate, succinates such as disodium succinate, acetate salts such as calcium acetate and sodium acetate, phosphoric salts such as sodium dihydrogen phosphate, disodium monohydrogen phosphate, sodium metaphosphate, trisodium phosphate, monobasic potassium phosphate, dibasic potassium phosphate, sodium polyphosphate, and sodium pyrophosphate, carbonates such as sodium carbonate, sodium bicarbonate, potassium carbonate, potassium bicarbonate, and ammonium carbonate, sodium sulfate, sodium sulfite, sodium bisulfite, calcium chloride, sodium chloride, potassium chloride, magnesium chloride, sodium hydroxide, and glutamate salts such as glutamic acid hydrochloride and monosodium glutamate monohydrate
D component: one or two or more kinds of acidic substances of pH 3.5 or lower selected from the group consisting of acidic polysaccharides such as alginic acid, amino polyvalent carboxylic acid such as glutamic acid and aspartic acid, saturated polyvalent carboxylic acid such as adipic acid and succinic acid, unsaturated polyvalent carboxylic acids such as fumaric acid, inorganic acid salts of amino polyvalent carboxylic acid such as glutamic acid hydrochloride, hydroxy polyvalent carboxylic acids such as tartaric acid, citric acid, and malic acid, and polymeric polyvalent carboxylic acids such as a methacrylic acid copolymer L.
2. For example, granulation is performed in accordance with a dry granulation method. Specifically, the resultant mixture is compression-molded by a compression molding device such as a ROLLER COMPACTOR or a tableting machine (slug machine), crushed and subjected to size adjustment by a particle sizing device such as a ROLL GRANULATOR or a sieve, to obtain a granulated substance. To the granulated substance, a cellulosic excipient such as crystalline cellulose, carmellose, carmellose calcium, carmellose sodium, croscarmellose sodium, carboxymethyl cellulose calcium, and low substituted hydroxypropylcellulose can also be added, and a disintegrant such as low substituted hydroxypropylcellulose, crystalline cellulose, hydroxypropyl starch, carmellose, carmellose calcium, carmellose sodium, potato starch, corn starch, low substituted hydroxypropylcellulose, crospovidone, croscarmellose sodium, and sodium carboxymethyl starch can also be added. To the granulated substance, a lubricant such as stearic acid, a stearic acid salt (a salt with metal such as aluminum, potassium, sodium, calcium, and magnesium), and sodium laurylsulfate can be added.

3. From the resulting granulated substance or a mixture of the granulated substance and an additive, a tablet (uncoated tablet) is obtained by pressing with a tableting machine. After the pressing into tablets, the resulting uncoated tablet may be coated with a coating agent such as hypromellose and Kollicoat IR.

EXAMPLES

Hereinafter, the present invention will be described in more detail with reference to Examples. The present invention is not limited by these Examples.

In the following Examples, an NMR spectrum was determined with JEOL JNM-EX400 nuclear magnetic resonance spectrometer using tetramethylsilane (TMS) as an internal standard. A MS spectrum was determined with JEOL JMS-T100LP and JMS-SX102A mass spectrometers. Elementary analysis was carried out with YANACO CHN CORDER MT-6 analyzer.

Reference Example 1

Bis(acetato-O)-[6,7-difluoro-1-(2-fluoroethyl)-8-methoxy-4-oxo-1,4-dihydroquinoline-3-carboxylato-$O^3,O^4$]boron 103 g (1.67 mol) of boric acid (for formation of catalyst) was added to 21.4 L (225 mol) of acetic anhydride under a nitrogen atmosphere, and the mixture was heated and stirred at 70.0 to 76.9° C. for 30 minutes (at a stirring rate of 69.5 rpm). The mixture was cooled to an inner temperature of 24.6° C., 1.01 kg (16.3 mol) of first additional boric acid was added, and the mixture was stirred at 24.6 to 27.4° C. for 30 minutes. 1.01 kg (16.3 mol) of second additional boric acid was added, and the mixture was stirred at 24.7 to 27.5° C. for 30 minutes. 1.01 kg (16.3 mol) of third additional boric acid was added, and the mixture was stirred at 24.7 to 27.7° C. for 30 minutes. 1.01 kg (16.3 mol) of fourth additional boric acid was added, and the mixture was stirred at 25.4 to 29.4° C. for 30 minutes. The mixture was further stirred at 50.0 to 56.9° C. for 30 minutes, to prepare a boric acid triacetate adjustment liquid. To the adjustment liquid, 5.50 kg (16.7 mol) of 6,7-difluoro-1-(2-fluoroethyl)-8-methoxy-4-oxo-1,4-dihydroquinoline-3-carboxylic acid ethyl ester was added, and the mixed liquid was stirred at 54.7 to 56.9° C. for 3 hours. The mixed liquid was cooled to 30.0° C., and allowed to stand at room temperature overnight. The mixed liquid was heated to 58.6° C. to dissolve the deposited compound, and 16.5 L of acetone was added to the mixed liquid to obtain a reaction liquid (a).

A mixed liquid of 193 L of water and 33.7 L (555 mol) of ammonia water (28%) was cooled to −0.6° C. under a nitrogen atmosphere. To the mixed liquid, the reaction liquid (a) was added, and the mixture was washed with 11.0 L of acetone. The mixture was cooled to 15.0° C., and stirred at 4.3 to 15.0° C. for 1 hour. The deposited crystal was collected by filtration, and the collected crystal was washed with 55.0 L of water to obtain 14.1 kg of crude wet crystal. The crude wet crystal was dried under reduced pressure at a setting temperature of 65.0° C. for about 22 hours to obtain 6.93 kg of crude crystal (yield: 96.7%).

To the crude crystal obtained, 34.7 L of acetone was added under a nitrogen atmosphere, and the mixture was heated (at hot water setting temperature of 57.0° C.) to dissolve the crude crystal. During the heating, 69.3 L of diisopropyl ether was added dropwise (added amount: 12.0 L) until crystallization. After confirmation of crystallization, the mixture was stirred at 48.3 to 51.7° C. for 15 minutes, the rest of diisopropyl ether was added dropwise, and the mixture was stirred at 45.8 to 49.7° C. for 15 minutes. The mixture was cooled to 15° C., and stirred at 6.5 to 15.0° C. for 30 minutes. The deposited crystal was collected by filtration, and the collected crystal was washed with 6.93 L of acetone and 13.9 L of diisopropyl ether, to obtain 7.41 kg of wet crystal. The wet crystal obtained was dried under reduced pressure at a setting temperature of 65.0° C. for about 20 hours to obtain 6.47 kg of bis(acetato-O)-[6,7-difluoro-1-(2-fluoroethyl)-8-methoxy-4-oxo-1,4-dihydroquinoline-3-carboxylato-$O^3,O^4$]boron (yield: 90.3%).

Elemental Analysis Value (%): as $C_{17}H_{15}BF_3NO_8$
Calcd.: C, 47.58; H, 3.52; N, 3.26.
Measured: C, 47.41; H, 3.41; N, 3.20.
$^1$H-NMR (CDCl$_3$, 400 MHz) δ: 2.04 (6H, s), 4.21 (3H, d, J=2.9 Hz), 4.88 (2H, dt, J=47.0, 4.4 Hz), 5.21 (2H, dt, J=24.9, 3.9 Hz), 8.17 (1H, t, J=8.8 Hz), 9.10 (1H, s).
ESI MS (positive) m/z: 430 (M+H)+.

Reference Example 2

Production of 7-[(3S,4S)-3-{(cyclopropylamino) methyl}-4-fluoropyrolidin-1-yl]-6-fluoro-1-(2-fluoroethyl)-8-methoxy-4-oxo-1,4-dihydroquinoline-3-carboxylic acid hydrochloride A mixed liquid of 3.56 kg (15.4 mol) of (3R,4S)-3-cyclopropylaminomethyl-4-fluoropyrolidine, 11.7 L (84.2 mol) of triethylamine, and 30.0 L of dimethylsulfoxide was stirred at 23.0 to 26.3° C. for 15 minutes under a nitrogen atmosphere. 6.00 kg (14.0 mol) of bis(acetato-O)-[6,7-difluoro-1-(2-fluoroethyl)-8-methoxy-4-oxo-1,4-dihydroquinoline-3-carboxylato-$O^3,O^4$]boron was added to the mixed liquid at 23.0 to 26.3° C. to obtain a reaction liquid. The reaction liquid was stirred at 23.7 to 26.3° C. for 2 hours. To the reaction liquid, 120 L of ethyl acetate was added, 120 L of water was added, a solution of 960 g (amount corresponding to 2 mol/L) of sodium hydroxide and 12.0 L of water was added, and the mixture was stirred for 5 minutes. After that, an aqueous layer was separated. To the aqueous layer, 120 L of ethyl acetate was added, and the mixture was stirred for 5 minutes. After that, an ethyl acetate layer was separated. The portions of the ethyl acetate layer were combined, 120 L of water was added, and the mixture was stirred for 5 minutes and allowed to stand. After that, an aqueous layer was removed. The ethyl acetate layer was distilled off under reduced pressure. The resultant residue was dissolved in 60.0 L of 2-propanol, and allowed to stand at room temperature overnight. A solution of 5.24 L (62.9 mol) of hydrochloric acid and 26.2 L (amount corresponding to 2 mol/L) of water was added to the solution, and the mixture was stirred at 28.2 to 30.0° C. for 30 minutes. The mixture was heated at an external temperature of 55.0° C. After dissolution (Dissolution was confirmed at 47.1° C., the mixture was cooled, resulting in crystallization. The mixture was stirred at 39.9 to 41.0° C. for 30 minutes, cooled (guide: to 20.0° C. at a setting temperature of 7.0° C., and to 20.0° C. or lower at −10.0° C.), and stirred at 2.2 to 10.0° C. for 1 hour. The deposited crystal was collected by filtration, and washed with 60 L of 2-propanol to obtain 9.57 kg of crude wet crystal of 7-{(3S,4S)-3-[(cyclopropylamino)methyl]-4-fluoropyrolidin-1-yl}-6-fluoro-1-(2-fluoroethyl)-8-methoxy-4-oxo-1,4-dihydroquinoline-3-carboxylic acid hydrochloride.

Reference Example 3

Method of producing 7-[(3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride A-type crystal (Compound 1)

9.57 kg of crude wet crystal of 7-{(3S,4S)-3-[(cyclopropylamino)methyl]-4-fluoropyrolidin-1-yl}-6-fluoro-1-(2-fluoroethyl)-8-methoxy-4-oxo-1,4-dihydroquinoline-3-carboxylic acid hydrochloride was added to a mixed liquid of 60 L of ethanol and 10.8 L of purified water, and dissolved by heating. This solution was passed through a filter, and washed with a mixed liquid of 24.0 L of ethanol and 1.20 L of purified water. When dissolution was confirmed, 96.0 L of heated ethanol (99.5) was added at 71.2 to 72.6° C.

The solution was cooled (hot water setting temperature: 60.0° C.) After crystallization was confirmed (crystallization temperature: 61.5° C.), the solution was stirred at 59.4 to 61.5° C. for 30 minutes. The solution was stepwisely cooled (to 50.0° C. at a hot water setting temperature of 40.0° C., to 40.0° C. at a hot water setting temperature of 30.0° C., to 30.0° C. at a hot water setting temperature of 20.0° C., to 20.0° C. at a setting temperature of 7.0° C., and to 15.0° C. at a setting temperature of −10.0° C., and then left to stand), and stirred at 4.8 to 10.0° C. for 1 hour. The deposited crystal was collected by filtration, and washed with 30.0 L of ethanol to obtain 5.25 kg of wet crystal of 7-{(3S,4S)-3-[(cyclopropylamino)methyl]-4-fluoropyrolidin-1-yl}-6-fluoro-1-(2-fluoroethyl)-8-methoxy-4-oxo-1,4-dihydroquinoline-3-carboxylic acid hydrochloride. The wet crystal obtained was dried under reduced pressure at a setting temperature of 50.0° C. for about 13 hours to obtain 4.83 kg of Compound 1 (yield: 72.6%).

FIG. 1 shows a result of X-ray powder diffraction of Compound 1 based on WO2013/069297. As understood from FIG. 1, peaks are found at 4.9°, 10.8°, 12.9°, 18.2°, 21.7°, 24.7°, and 26.4°, and characteristic peaks are confirmed at 10.8°, 12.9°, and 24.7°.

Elementary Analysis Value (%): as $C_{21}H_{24}F_3N_3O_4HCl$
Calcd.: C, 53.00; H, 5.30; N, 8.83.
Measured: C, 53.04; H, 5.18; N, 8.83.
$^1$H NMR (DMSO-$d_6$, 400 MHz) δ (ppm): 0.77-0.81 (2H, m), 0.95-1.06 (2H, m), 2.80-2.90 (2H, m), 3.21-3.24 (1H, m), 3.35-3.39 (1H, m), 3.57 (3H, s), 3.65-3.78 (3H, m), 4.13 (1H, dd, J=41.8, 13.1 Hz), 4.64-4.97 (3H, m), 5.14 (1H, dd, J=32.7, 15.6 Hz), 5.50 (1H, d, J=53.7 Hz), 7.80 (1H, d, J=13.7 Hz), 8.86 (1H, s), 9.44 (2H, brs), 15.11 (1H, brs).
ESI MS (positive) m/z: 440 (M+H)+.

Example 1

In accordance with prescription in Table 2, Compound 1 crushed for 45 seconds using Wonder Blender (WB-1, manufactured by OSAKA CHEMICAL Co., Ltd.), and L-glutamic acid hydrochloride were mixed for 3 minutes using a pestle and a mortar. The mixture and crystalline cellulose were mixed for 3 minutes in a polyethylene bag. To the mixture, sodium stearyl fumarate was added, and the mixture was mixed in the polyethylene bag for 30 seconds. The mixture was compression-molded using a tableting machine (HT-AP-18SS-II, manufactured by HATA TEKKOSHO CO., LTD., diameter of mortar: 8.5 mm, punch with a R plane having a curvature radius of 10 mm) so that the mass was 200 mg, and crushed by hand, to obtain a granulated substance. Of the resulting granulated substance, the granulated substance which was passed through a sieve with an opening of 850 μm, and left on a sieve with an opening of 106 μm was obtained as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 30 seconds. The mixture was pressed into a tablet using a tableting machine (HT-AP-18SS-II, manufactured by HATA TEKKOSHO CO., LTD., diameter of mortar: 8.5 mm, punch with a R plane having a curvature radius of 10 mm) so that the mass was 250 mg and the thickness of a tablet was 4.2 mm, to obtain a tablet (uncoated tablet).

Example 2

In accordance with prescription in Table 2, the same operation as in Example 1 was performed except that monobasic sodium citrate was used instead of L-glutamic acid hydrochloride.

Example 3

In accordance with prescription in Table 2, the same operation as in Example 1 was performed except that dibasic sodium citrate was used instead of L-glutamic acid hydrochloride.

Comparative Example 1

In accordance with prescription in Table 2, Compound 1 crushed for 45 seconds using Wonder Blender (WB-1, manufactured by OSAKA CHEMICAL Co., Ltd.), and crystalline cellulose were mixed for 3 minutes in a polyethylene bag. To the mixture, sodium stearyl fumarate was added, and the mixture was mixed in the polyethylene bag for 30 seconds. The mixture was compression-molded using a tableting machine (HT-AP-18SS-II, manufactured by HATA TEKKOSHO CO., LTD., diameter of mortar: 8.5 mm, punch with a R plane having a curvature radius of 10 mm) so that the mass was 200 mg, and crushed by hand, to obtain a granulated substance. Of the resulting granulated substance, the granulated substance which was passed through a sieve with an opening of 850 μm, and left on a sieve with an opening of 106 μm was obtained as main drug granules. The main drug granules, crystalline cellulose, and low substituted hydroxypropylcellulose n were then mixed for 3 minutes in a polyethylene bag. To the mixture, magnesium stearate was added, and the mixture was mixed in the polyethylene bag for 30 seconds. The mixture was pressed into a tablet using a tableting machine (HT-AP-18SS-II, manufactured by HATA TEKKOSHO CO., LTD., diameter of mortar: 8.5 mm, punch with a R plane having a curvature radius of 10 mm) so that the mass was 250 mg and the thickness of a tablet was 4.2 mm, to obtain a tablet.

TABLE 2

| COMPONENT | EXAMPLE 1 | EXAMPLE 2 | EXAMPLE 3 | COMPARATIVE EXAMPLE 1 |
|---|---|---|---|---|
| COMPOUND 1 | 108.3 | 108.3 | 108.3 | 108.3 |
| L-GLUTAMIC ACID HYDROCHLORIDE | 21.6 | — | — | — |
| MONOBASIC SODIUM CITRATE | — | 21.6 | — | — |
| DIBASIC SODIUM CITRATE | — | — | 21.6 | — |
| CRYSTALLINE CELLULOSE | 17.1 | 17.1 | 17.1 | 38.7 |
| MAGNESIUM STEARATE | — | — | — | — |
| SODIUM STEARYL FUMARATE | 3 | 3 | 3 | 3 |
| SUBTOTAL (mg) | 150 | 150 | 150 | 150 |
| CRYSTALLINE CELLULOSE* | 73.2 | 73.2 | 73.2 | 73.2 |
| LOW SUBSTITUTED HYDROXYPROPYLCELLULOSE | 25 | 25 | 25 | 25 |
| MAGNESIUM STEARATE* | 1.8 | 1.8 | 1.8 | 1.8 |
| TOTAL (mg) | 250 | 250 | 250 | 250 |

*Added after granulation

Test Example 1

Dissolution Test (First Fluid for Dissolution Test)

Figure 2:
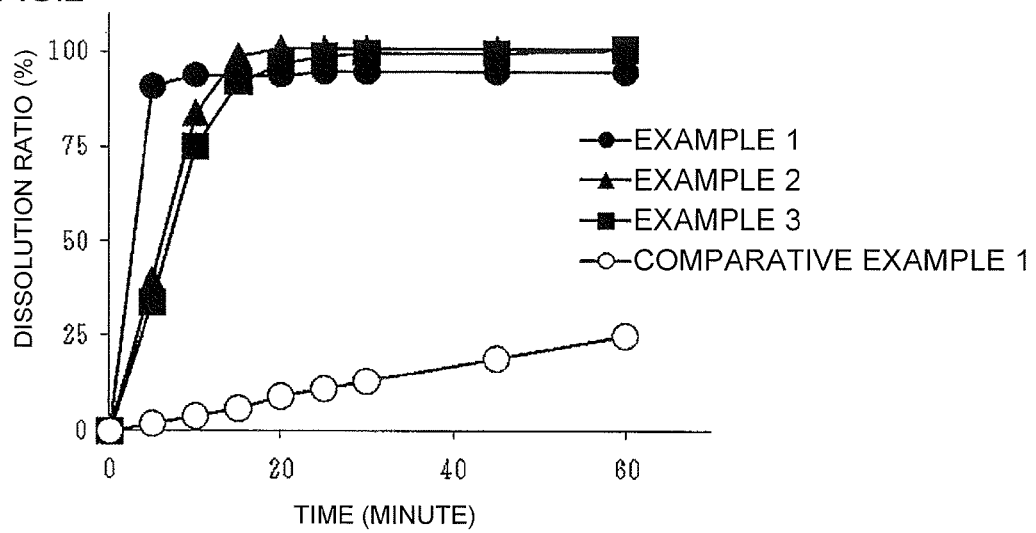
FIG. 2 shows results of dissolution test of tablets immediately after production in Examples 1 to 3 and Comparative Example 1 (dissolution media: first fluid for dissolution test).

In order to evaluate each of the compositions (tablet) in Examples and Comparative Examples, a dissolution test was performed in accordance with dissolution apparatus 2 in the Japanese Pharmacopoeia Sixteenth Edition (paddle method). Detailed conditions of the dissolution test are as follows. The results of the dissolution test are shown in FIG. 2.

Paddle rotation speed: 50 rpm
Temperature of the dissolution medium: 37° C.
Dissolution media: the Japanese Pharmacopoeia Sixteenth Edition, first fluid for dissolution test, 900 mL In the tablet in Comparative Example 1 in which a salting-out agent was not contained, the dissolution property is very poor, and the dissolution ratio after 60 minutes is 25% or less. This is considered because Compound 1 on a surface of the tablet is gelled by contact with water, and rapid permeation of water into the inside of the tablet is suppressed. When the residue after the dissolution test was observed, it was visually confirmed that a dissolution media was not permeated into the inside of the tablet, and disintegration of the tablet was not caused.

In contrast, in the tablets in Examples 1 to 3 in which L-glutamic acid hydrochloride (Example 1), monobasic sodium citrate (Example 2), or dibasic sodium citrate (Example 3) was contained as a salting-out agent, the dissolution ratio was significantly improved. In all the tablets in Examples 1 to 3, the dissolution ratio after 10 minutes exhibited 70% or more, and the dissolution ratio after 60 minutes exhibited about 90% (FIG. 2). Since L-glutamic acid hydrochloride has a pH of 3.5 or lower, L-glutamic acid hydrochloride acts as a salting-out agent and an acidic substance of pH 3.5 or lower.

Example 4

In accordance with prescription in Table 3, Compound 1, 1 mg of L-glutamic acid hydrochloride which was crushed and then passed through a sieve with an opening of 212 μm, monobasic sodium citrate passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation speed: 3 min$^1$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with a R plane having a curvature radius of 10 mm) so that the mass was 250 mg and the thickness of a tablet was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION) as an aqueous coating.

Example 5

In accordance with prescription in Table 3, the same operation as in Example 4 was performed.

Example 6

In accordance with prescription in Table 3, the same operation as in Example 4 was performed.

Example 7

In accordance with prescription in Table 3, Compound 1, monobasic sodium citrate passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation speed: 3 min$^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with a R plane having a curvature radius of 10 mm) so that the mass was 250 mg and the thickness of a tablet was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION) as an aqueous coating.

TABLE 3

| COMPONENT | EXAMPLE 4 | EXAMPLE 5 | EXAMPLE 6 | EXAMPLE 7 |
|---|---|---|---|---|
| COMPOUND 1 | 108.3 | 108.3 | 108.3 | 108.3 |
| L-GLUTAMIC ACID HYDROCHLORIDE | 1 | 3 | 7.2 | — |
| MONOBASIC SODIUM CITRATE | 21.6 | 21.6 | 21.6 | 21.6 |
| CRYSTALLINE CELLULOSE | 16.85 | 14.85 | 10.65 | 17.85 |
| MAGNESIUM STEARATE | 2.25 | 2.25 | 2.25 | 2.25 |
| SUBTOTAL (mg) | 150 | 150 | 150 | 150 |
| CRYSTALLINE CELLULOSE* | 73.75 | 73.75 | 73.75 | 73.75 |
| LOW SUBSTITUTED HYDROXYPROPYLCELLULOSE | 25 | 25 | 25 | 25 |
| MAGNESIUM STEARATE* | 1.25 | 1.25 | 1.25 | 1.25 |
| SUBTOTAL (mg) | 250 | 250 | 250 | 250 |
| HYPROMELLOSE | 5 | 5 | 5 | 5 |
| TITANIUM OXIDE | 2.5 | 2.5 | 2.5 | 2.5 |
| POLYETHYLENE GLYCOL 400 | 0.5 | 0.5 | 0.5 | 0.5 |
| TOTAL (mg) | 258 | 258 | 258 | 258 |

*Added after granulation

Test Example 2

Stability Test

Each of the compositions (tablets) in Examples 4 to 7 was placed in a glass bottle, and stored in a sealed state at 40° C. for 4 weeks. The content of 7-{(3S,4S)-3-aminomethyl-4-fluoropyrolidin-1-yl}-6-fluoro-1-(2-fluoroethyl)-8-methoxy-4-oxo-1,4-dihydroquinoline-3-carboxylic acid (Compound 2) and the content of Compound 1 after the storage were measured through liquid chromatography, and the content of Compound 2 was represented as a percentage based on the content of Compound 1. As a test condition by liquid chromatography, test condition 1 was used.
(Test Condition 1)
Column: a separation column in which each stainless tube with an inner diameter of 4.6 mm and a length of 150 mm was charged with octadecyl-silylated silica gel of 3 μm for liquid chromatography (GL Sciences Inc., Inertsil ODS-3).
A liquid: a liquid in which 2.16 g of sodium 1-octane-sulfonate was dissolved in diluted phosphoric acid (1→1,000) in a volume of 1,000 mL.
B liquid: methanol for liquid chromatography
Liquid sending: The mixed ratio of A liquid and B liquid was changed to control the concentration gradient.
Detector: UV absorption spectrophotometer (measurement wavelength: 294 nm)
Retention time of Compound 2 with respect to Compound 1: 0.69

The results of stability test are shown in Table 4. In the tablets which contained L-glutamic acid hydrochloride as an acidic substance of pH 3.5 or lower (Examples 4 to 6), Compound 2 was hardly produced and the stabilization effect was higher as compared with the tablet in which the acidic substance of pH 3.5 or lower was not contained (Example 7).

TABLE 4

| ITEM | EXAMPLE 4 | EXAMPLE 5 | EXAMPLE 6 | EXAMPLE 7 |
|---|---|---|---|---|
| CONTENT OF COMPOUND 2 AFTER STORAGE AT 40° C./75% RH FOR 4 WEEKS (SEALED STATE) % | 0.01 | 0.01 | 0.01 | 0.07 |

Figure 3:
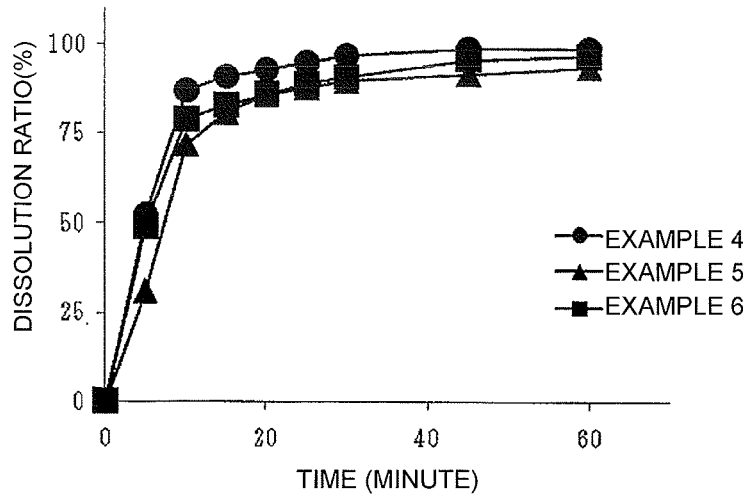
FIG. 3 shows results of dissolution test of tablets immediately after production in Examples 4 to 6 (dissolution media: first fluid for dissolution test).

The tablets obtained in Examples 4 to 6 contain monobasic sodium citrate as a salting-out agent. Therefore, when an dissolution test is performed under the condition of Test Example 1 (first liquid for dissolution test) in the same manner as in Examples 1 to 3, the effect of significantly improving the dissolution ratio is recognized (FIG. 3). Whether or not the effect of improving the dissolution ratio even when a dissolution medium in the dissolution test was water was confirmed.

Test Example 3

Dissolution Test (Immediately after Production, Water)

Figure 4:
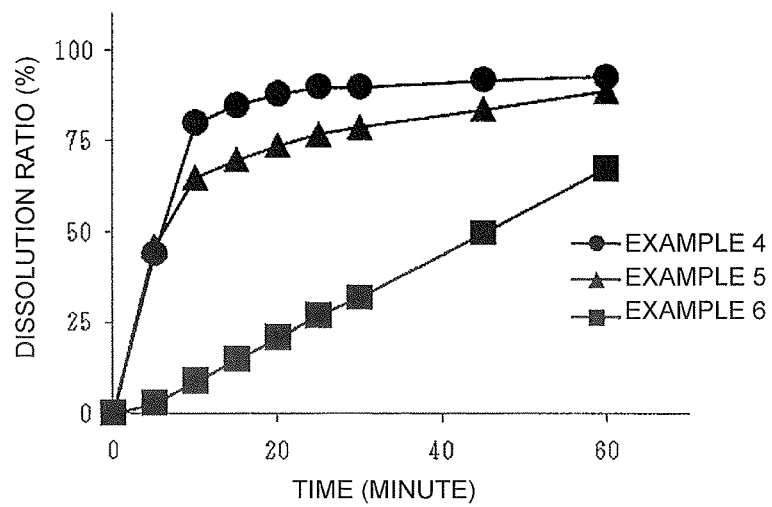
FIG. 4 shows results of dissolution test of the tablets immediately after production in Examples 4 to 6 (dissolution media: water).

For the tablets obtained in Examples 4 to 6, the dissolution test was performed in accordance with dissolution apparatus 2 in the Japanese Pharmacopoeia Sixteenth Edition (paddle method). Detailed conditions of the dissolution test are as follows. The results of the dissolution test are shown in FIG. 4.
Paddle rotation speed: 50 rpm
Temperature of the dissolution medium: 37° C.
Dissolution media: the Japanese Pharmacopoeia Sixteenth Edition, water, 900 mL
In all the tablets in Examples 4 to 6, the dissolution ratio after 60 minutes was more than 50%. In Example 4 using 1.0 mg of L-glutamic acid hydrochloride and Example 5 using 3.0 mg of L-glutamic acid hydrochloride, the initial dissolution is earlier than that in Example 6 using 7.2 mg of L-glutamic acid hydrochloride, and the dissolution ratio after 10 minutes is about 60%. (FIG. 4)

Test Example 4

Dissolution Test (after Storage Under Acceleration Condition, First Liquid for Dissolution Test)

Figure 5:
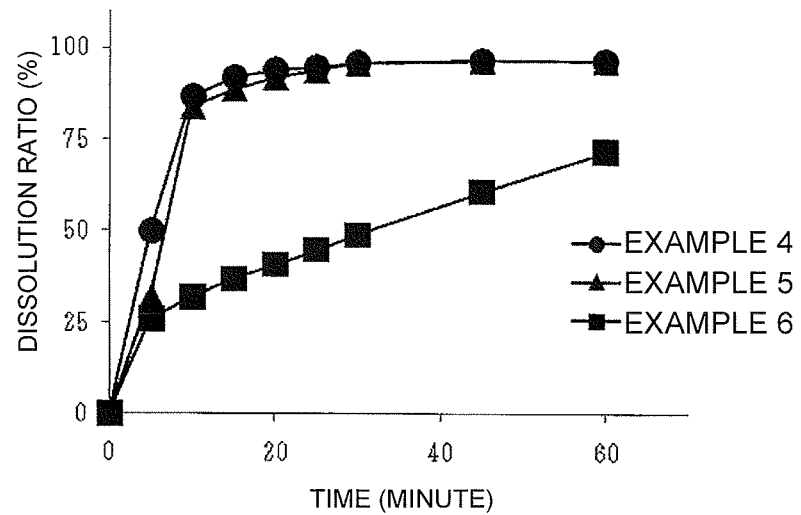
FIG. 5 shows results of dissolution test of the tablets in Examples 4 to 6 after storage under conditions of acceleration and opened state (dissolution media: first fluid for dissolution test).
Figure 6:
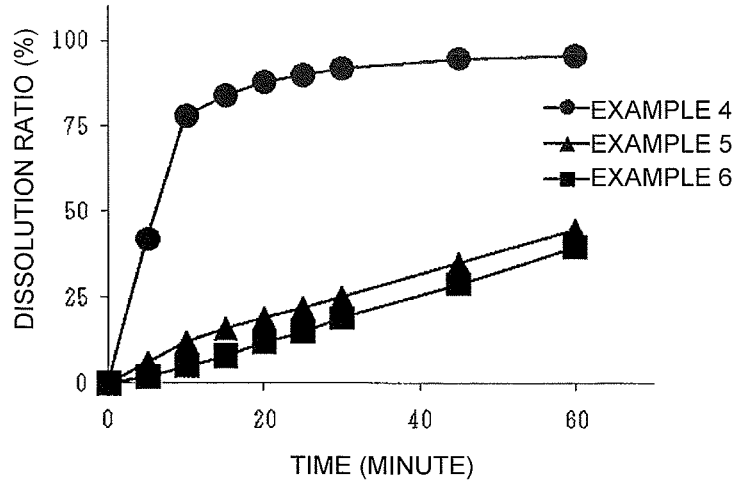
FIG. 6 shows results of dissolution test of the tablets in Examples 4 to 6 after storage under conditions of acceleration and sealed state (dissolution media: first fluid for dissolution test).

Each of the tablets in Examples 4 to 6 was placed in a glass bottle, and stored in an opened state and a sealed state under an acceleration condition (40° C./75% RH) for 4 weeks. The stored tablet was subjected to a dissolution test in the same manner as in Test Example 1 (dissolution media: first fluid for dissolution test). The results of the dissolution test are shown in FIGS. 5 (opened state) and 6 (sealed state).

In a case of storage under the acceleration condition, the dissolution ratio tended to decrease. However, in Example 4 (1.0 mg of L-glutamic acid hydrochloride), the dissolution ratio did not decrease even under the opened condition and the sealed condition. In Example 5 (3.0 mg of L-glutamic acid hydrochloride), the dissolution ratio did not decrease under the opened condition.

Example 8

In accordance with prescription in Table 5, Compound 1, alginic acid passed through a sieve with an opening of 212 μm, monobasic sodium citrate passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation speed: 3 $\min^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with a R plane having a curvature radius of 10 mm) so that the mass was 250 mg and the thickness of a tablet was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION) as an aqueous coating.

Example 9

The same operation as in Example 8 except that L-glutamic acid hydrochloride was used instead of alginic acid was performed.

Example 10

In accordance with prescription in Table 5, Compound 1, monobasic sodium citrate passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation speed: 3 $\min^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with a R plane having a curvature radius of 10 mm) so that the mass was 250 mg and the thickness of a tablet was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION) as an aqueous coating.

TABLE 5

| COMPONENT | EXAMPLE 8 | EXAMPLE 9 | EXAMPLE 10 |
|---|---|---|---|
| COMPOUND 1 | 108.3 | 108.3 | 108.3 |
| ALGINIC ACID | 7.2 | — | — |
| L-GLUTAMIC ACID HYDROCHLORIDE | — | 7.2 | — |
| MONOBASIC SODIUM CITRATE | 21.6 | 21.6 | 21.6 |
| CRYSTALLINE CELLULOSE | 10.65 | 10.65 | 17.85 |
| MAGNESIUM STEARATE | 2.25 | 2.25 | 2.25 |
| SUBTOTAL (mg) | 150 | 150 | 150 |
| CRYSTALLINE CELLULOSE* | 73.75 | 73.75 | 73.75 |
| LOW SUBSTITUTED HYDROXYPROPYLCELLULOSE | 25 | 25 | 25 |
| MAGNESIUM STEARATE* | 1.25 | 1.25 | 1.25 |
| HYPROMELLOSE | 5 | 5 | 5 |
| TITANIUM OXIDE | 2.5 | 2.5 | 2.5 |
| POLYETHYLENE GLYCOL 400 | 0.5 | 0.5 | 0.5 |
| TOTAL (mg) | 258 | 258 | 258 |

*Added after granulation

Test Example 5

Dissolution Test (Immediately after Production, Water)

Figure 7:
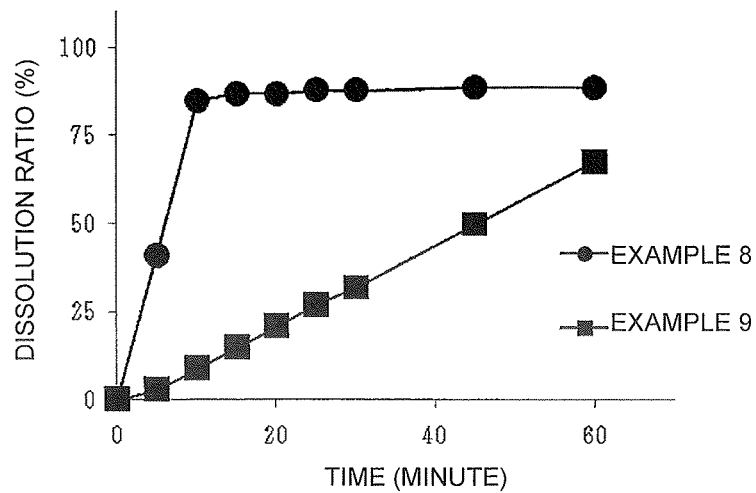
FIG. 7 shows results of dissolution test of tablets immediately after production in Examples 8 and 9 (dissolution media: water).

The compositions (tablets) obtained in Examples 8 and 9 were subjected to a dissolution test in the same manner as in Test Example 3. The results of the dissolution test are shown in FIG. 7. In Example 8 using alginic acid of which the solubility in water at 20° C. is less than 10%, the dissolution ratio is higher than that in Example 9 using L-glutamic acid hydrochloride of which the solubility in water at 20° C. is 10% or more. In a case of using L-glutamic acid hydrochloride of which the solubility in water at 20° C. is 10% or more, an increase in the use amount tends to decrease the dissolution ratio in water (FIG. 4). However, even when alginic acid is used in an amount as relatively large as 7.2 mg, high dissolution ratio is maintained.

Test Example 6

Stability Test

Each of the compositions (tablets) obtained in Examples 8 and 10 was placed in a glass bottle, and stored in a sealed state at 40° C. for 4 weeks. The content of Compound 2 and the content of Compound 1 after the storage were measured through liquid chromatography, and the content of Compound 2 was represented as a percentage relative to the content of Compound 1. As a test condition by liquid chromatography, the test condition 1 was used.

The results of the stability test are shown in Table 6. In the tablet which contained alginic acid (Example 8), Compound 2 was hardly produced and the stabilization effect was higher as compared with the tablet in which alginic acid was not contained and the acidic substance of pH 3.5 or lower was not contained (Example 10).

TABLE 6

| ITEM | EXAMPLE 8 | EXAMPLE 10 |
|---|---|---|
| CONTENT OF COMPOUND 2 AFTER STORAGE AT 40° C./75% RH FOR 4 WEEKS (SEALED STATE) % | 0.03 | 0.07 |

Example 11

In accordance with prescription in Table 7, Compound 1, monobasic sodium citrate passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation speed: 3 min$^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. Next, the granules, tartaric acid passed through a sieve with an opening of 212 μm, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with a R plane having a curvature radius of 10 mm) so that the mass was 250 mg and the thickness of a tablet was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION) as an aqueous coating.

Example 12

A tablet was produced in the same manner as in Example 11 except that tartaric acid was changed into citric acid.

TABLE 7

| COMPONENT | EXAMPLE 11 | EXAMPLE 12 |
|---|---|---|
| COMPOUND 1 | 108.3 | 108.3 |
| MONOBASIC SODIUM CITRATE | 21.6 | 21.6 |
| CRYSTALLINE CELLULOSE | 17.85 | 17.85 |
| MAGNESIUM STEARATE | 2.25 | 2.25 |
| SUBTOTAL (mg) | 150 | 150 |
| TARTARIC ACID | 7.2 | — |
| CITRIC ACID | — | 7.2 |
| CRYSTALLINE CELLULOSE* | 66.55 | 66.55 |
| LOW SUBSTITUTED HYDROXYPROPYLCELLULOSE | 25 | 25 |
| MAGNESIUM STEARATE* | 1.25 | 1.25 |
| HYPROMELLOSE | 5 | 5 |

TABLE 7-continued

| COMPONENT | EXAMPLE 11 | EXAMPLE 12 |
|---|---|---|
| TITANIUM OXIDE | 2.5 | 2.5 |
| POLYETHYLENE GLYCOL 400 | 0.5 | 0.5 |
| TOTAL (mg) | 258 | 258 |

*Added after granulation

Test Example 7

Dissolution Test (First Liquid for Dissolution Test)

Figure 8:
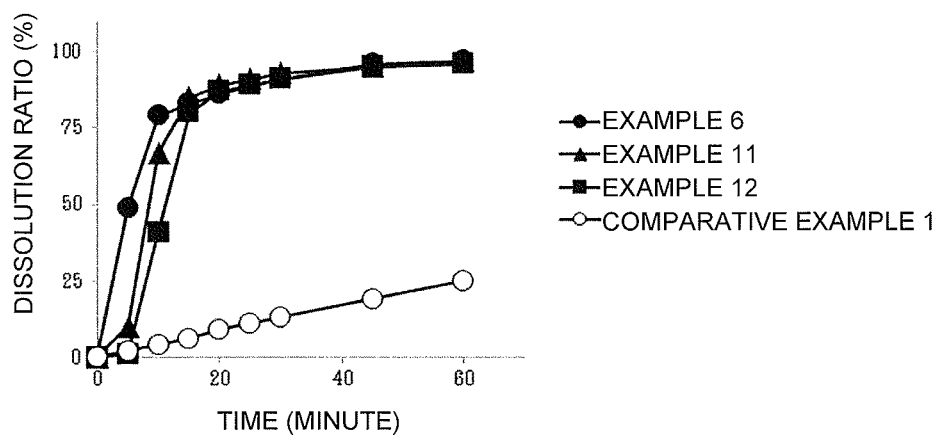
FIG. 8 shows results of dissolution test of tablets immediately after production in Examples 6, 11, and 12, and Comparative Example 1 (dissolution media: first fluid for dissolution test).

In order to evaluate each of the compositions (tablets) in Examples 6, 11, and 12 and Comparative Example 1, a dissolution test was performed in the same manner as in Test Example 1. The results of the dissolution test are shown in FIG. 8.

Like L-glutamic acid hydrochloride, tartaric acid and citric acid are an acidic substance having a solubility in water at 20° C. of 10% or more and a pH of 3.5 or lower. In all the tablet in Example 11 using tartaric acid and the tablet in Example 12 using citric acid, improvement of dissolution ratio was recognized, like the tablet in Example 6.

Example 13

In accordance with prescription in Table 8, Compound 1, alginic acid and monobasic sodium citrate passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation speed: 3 min$^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 7.5 mm, punch with a R plane having a curvature radius of 9 mm) so that the mass was 190 mg and the thickness of a tablet was 3.9 mm, to obtain an uncoated tablet. The uncoated tablet was coated with a mixture of hypromellose, titanium oxide, polyethylene glycol 400, and yellow ferric oxide using a Hicoater (HCT-MINI manufactured by FREUND CORPORATION) as an aqueous coating.

Examples 14 and 15

Tablets were produced in the same manner as in Example 13 except that the use amount of alginic acid was changed into amounts described in Table 8.

TABLE 8

| COMPONENT | EXAMPLE 13 | EXAMPLE 14 | EXAMPLE 15 |
|---|---|---|---|
| COMPOUND 1 | 81.2 | 81.2 | 81.2 |
| ALGINIC ACID | 5.4 | 2.4 | — |
| MONOBASIC SODIUM CITRATE | 16.2 | 16.2 | 16.2 |
| CRYSTALLINE CELLULOSE | 8 | 11 | 13.4 |
| MAGNESIUM STEARATE | 1.7 | 1.7 | 1.7 |
| SUBTOTAL (mg) | 112.5 | 112.5 | 112.5 |
| CRYSTALLINE CELLULOSE* | 56.5 | 56.5 | 56.5 |
| LOW SUBSTITUTED HYDROXYPROPYLCELLULOSE | 20 | 20 | 20 |
| MAGNESIUM STEARATE* | 1 | 1 | 1 |
| HYPROMELLOSE | 3.6 | 3.6 | 3.6 |
| TITANIUM OXIDE | 1.96 | 1.96 | 1.96 |
| POLYETHYLENE GLYCOL 400 | 0.36 | 0.36 | 0.36 |
| YELLOW FERRIC OXIDE | 0.08 | 0.08 | 0.08 |
| TOTAL (mg) | 196 | 196 | 196 |

*Added after granulation

Test Example 8

Dissolution Test (Immediately after Production, Water)

Figure 9:
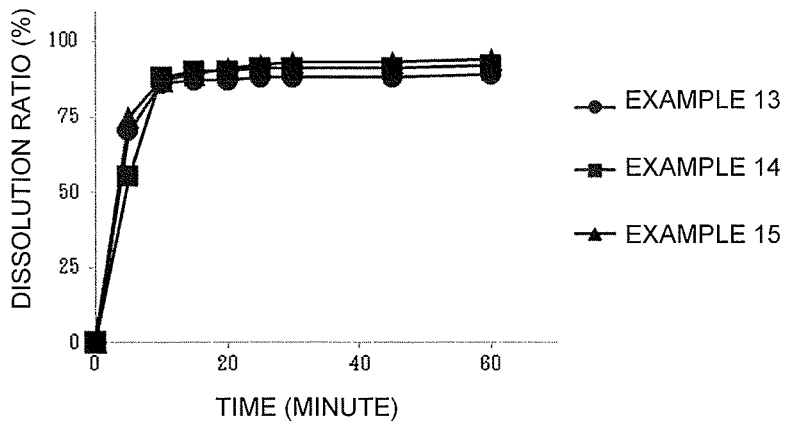
FIG. 9 shows results of dissolution test of tablets immediately after production in Examples 13 to 15 (dissolution media: water).

The tablets obtained in Examples 13 to 15 were subjected to a dissolution test in the same manner as in Test Example 3. The results of the dissolution test are shown in FIG. 9.

In all the tablets in Examples 13 to 15, the dissolution ratio after 60 minutes was more than 85%, and good improvement of the dissolution ratio was recognized. As understood from FIG. 9, when an acidic substance having a solubility in water at 20° C. of less than 10% and a pH of 3.5 or lower, like alginic acid, was used, good dissolution ratio was exhibited regardless of the content.

Example 16

In accordance with prescription in Table 9, Compound 1, L-aspartic acid passed through a sieve with an opening of 212 μm, monobasic sodium citrate passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation speed: 3 $min^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with a R plane having a curvature radius of 10 mm) so that the mass was 250 mg and the thickness of a tablet was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION) as an aqueous coating.

Example 17

A tablet was produced in the same manner as in Example 16 except that L-aspartic acid was changed into adipic acid.

Example 18

A tablet was produced in the same manner as in Example 16 except that L-aspartic acid was changed into succinic acid.

Example 19

A tablet was produced in the same manner as in Example 16 except that L-aspartic acid was changed into a methacrylic acid polymer L.

TABLE 9

| COMPONENT | EXAMPLE 16 | EXAMPLE 17 | EXAMPLE 18 | EXAMPLE 19 |
|---|---|---|---|---|
| COMPOUND 1 | 108.3 | 108.3 | 108.3 | 108.3 |
| L-ASPARTIC ACID | 7.2 | — | — | — |
| ADIPIC ACID | — | 7.2 | — | — |
| SUCCINIC ACID | — | — | 7.2 | — |
| METHACRYLIC ACID COPOLYMER L | — | — | — | 7.2 |
| MONOBASIC SODIUM CITRATE | 21.6 | 21.6 | 21.6 | 21.6 |
| CRYSTALLINE CELLULOSE | 10.65 | 10.7 | 10.7 | 10.7 |
| MAGNESIUM STEARATE | 2.25 | 2.2 | 2.2 | 2.2 |
| SUBTOTAL (mg) | 150 | 150 | 150 | 150 |
| CRYSTALLINE CELLULOSE* | 73.75 | 73.8 | 73.8 | 73.8 |
| LOW SUBSTITUTED HYDROXYPROPYL-CELLULOSE | 25 | 25 | 25 | 25 |
| MAGNESIUM STEARATE* | 1.25 | 1.2 | 1.2 | 1.2 |
| HYPROMELLOSE | 5 | 4.8 | 4.8 | 4.8 |
| TITANIUM OXIDE | 2.5 | 2.62 | 2.62 | 2.62 |
| POLYETHYLENE GLYCOL 400 | 0.5 | 0.48 | 0.48 | 0.48 |
| YELLOW FERRIC OXIDE | — | 0.1 | 0.1 | 0.1 |
| TOTAL (mg) | 258 | 258 | 258 | 1.96 |

*Added after granulation

Test Example 9

Dissolution Test (Immediately after Production, Water)

Figure 10:
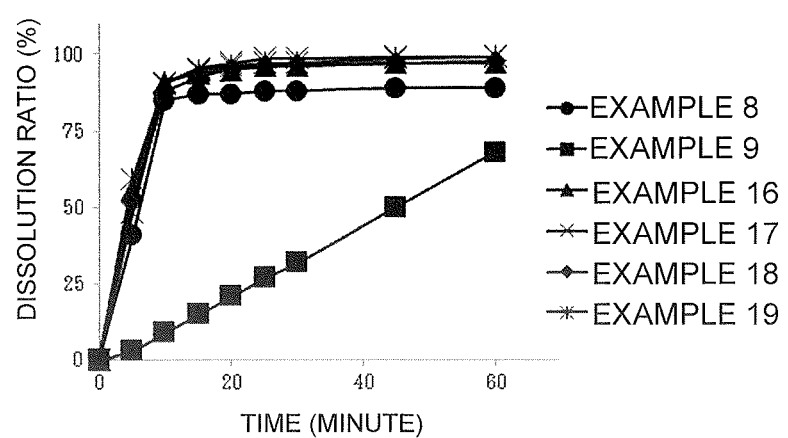
FIG. 10 shows results of dissolution test of tablets immediately after production in Examples 8, 9, and 16 to 19 (dissolution media: water).

The tablets obtained in Examples 8, 9, and 16 to 19 were subjected to a dissolution test in the same manner as in Test Example 3. The results of the dissolution test are shown in FIG. 10.

Like alginic acid, all L-aspartic acid, adipic acid, succinic acid, and a methacrylic acid copolymer L are each an acidic substance having a solubility in water at 20° C. of less than 10% and a pH of 3.5 or lower. In the tablets produced in Examples 8, and 16 to 19 produced using such an acidic substance, better improvement of dissolution ratio was recognized than that in Example 9 (tablet in which an acidic substance having a solubility in water at 20° C. of 10% or more was added in an amount more than 0.05 parts by mass relative to Compound 1 (1 part by mass)).

INDUSTRIAL APPLICABILITY

When a solid pharmaceutical composition which contains the compound of the formula (1) or a salt thereof contains a cellulosic excipient, and a salting-out agent, the solid pharmaceutical composition in which the dissolution property is improved can be provided.

The invention claimed is:

1. A solid pharmaceutical composition comprising 7-[(3S, 4S)-3-{(cyclopropylamino)methy}-4-fluoropyrolidin-1-yl]-6-fluoro-1-(2-fluoroethyl)-8-methoxy-4-oxo-1,4-dihydroquinoline-3-carboxylic acid or a salt thereof, a cellulosic excipient, and a salting-out agent,
    wherein the salting-out agent is at least one compound selected from the group consisting of an inorganic acid salt, a citric salt, a succinate salt, an acetate salt and a glutamate salt.

2. The solid pharmaceutical composition according to claim 1, further comprising an acidic substance having a pH of 3.5 or lower.

3. The solid pharmaceutical composition according to claim 2, wherein the acidic substance has a solubility in water at 20° C. of less than 10%.

4. The solid pharmaceutical composition according to claim 3, wherein the acidic substance having a solubility in water at 20° C. of less than 10% is at least one compound selected from the group consisting of alginic acid, glutamic acid, aspartic acid, adipic acid, succinic acid, a methacrylic acid copolymer L, and fumaric acid.

5. The solid pharmaceutical composition according to claim 2, wherein the acidic substance has a solubility in water at 20° C. of 10% or more.

6. The solid pharmaceutical composition according to claim 5, wherein the acidic substance having a solubility in water at 20° C. of 10% or more is at least one compound selected from the group consisting of glutamic acid hydrochloride, tartaric acid, citric acid, and malic acid.

7. The solid pharmaceutical composition according to claim 5, wherein the acidic substance having a solubility in water at 20° C. of 10% or more is a compound different from the salting-out agent, and a ratio of the acidic substance is 0.001 parts by mass or more and 0.05 parts by mass or less relative to 1 part by mass of the 7-[(3S,4S)-3-{(cyclopropylamino)methy}-4-fluoropyrolidin-1-yl]-6-fluoro-1-(2-fluoroethyl)-8-methoxy-4-oxo-1,4-dihydroquinoline-3-carboxylic acid or salt thereof.

8. The solid pharmaceutical composition according to claim 1, wherein the salting-out agent is at least one compound selected from the group consisting of monobasic sodium citrate, dibasic sodium citrate, sodium citrate, disodium succinate, calcium acetate, sodium acetate, sodium dihydrogen phosphate, disodium monohydrogen phosphate, sodium metaphosphate, trisodium phosphate, monobasic potassium phosphate, dibasic potassium phosphate, sodium polyphosphate, sodium pyrophosphate, sodium carbonate, sodium bicarbonate, potassium carbonate, potassium bicarbonate, ammonium carbonate, sodium sulfate, sodium sulfite, sodium bisulfite, calcium chloride, sodium chloride, potassium chloride, magnesium chloride, sodium hydroxide, L-glutamic acid hydrochloride, and monosodium glutamate monohydrate.

9. The solid pharmaceutical composition according to claim 1, wherein the salting-out agent is a citric salt.

10. The solid pharmaceutical composition according to claim 1, wherein the salting-out agent is monobasic sodium citrate.

11. The solid pharmaceutical composition according to claim 2, wherein the salting-out agent is monobasic sodium citrate and the acidic substance is glutamic acid hydrochloride, and wherein a ratio of the glutamic acid hydrochloride is 0.02 parts by mass or more and 0.20 parts by mass or less relative to 1 part by mass of the monobasic sodium citrate.

12. The solid pharmaceutical composition according to claim 2, comprising glutamic acid hydrochloride as the salting-out agent and the acidic substance.

13. The solid pharmaceutical composition according to claim 1, which is obtained by mixing the 7-[(3S,4S)-3-{(cyclopropylamino)methy}-4-fluoropyrolidin-1-yl]-6-fluoro-1-(2-fluoroethyl)-8-methoxy-4-oxo-1,4-dihydroquinoline-3-carboxylic acid or salt thereof, the cellulosic excipient, and the salting-out agent to obtain a mixture, and then granulating the mixture through a dry granulation method.

14. The solid pharmaceutical composition according to claim 1, wherein the cellulosic excipient is crystalline cellulose.

15. The solid pharmaceutical composition according to claim 1, comprising 7-[(3S,4S)-3-{(cyclopropylamino)methy}-4-fluoropyrolidin-1-yl]-6-fluoro-1-(2-fluoroethyl)-8-methoxy-4-oxo-1,4-dihydroquinoline-3-carboxylic acid hydrochloride.

* * * * *